(12) United States Patent
Vetter et al.

(10) Patent No.: US 11,751,900 B2
(45) Date of Patent: Sep. 12, 2023

(54) THROMBO-EMBOLIC PROTECTION AND EMBOLECTOMY/THROMBECTOMY DEVICES AND METHODS

(71) Applicant: Transmed7, LLC, Portola Valley, CA (US)

(72) Inventors: James W Vetter, Portola Valley, CA (US); Eugene H Vetter, Portola Valley, CA (US)

(73) Assignee: TransMed7, LLC, Portola Valley, CA (US)

( * ) Notice: Subject to any disclaimer, the term of this patent is extended or adjusted under 35 U.S.C. 154(b) by 396 days.

(21) Appl. No.: 16/566,347

(22) Filed: Sep. 10, 2019

(65) Prior Publication Data

US 2020/0146709 A1 May 14, 2020

Related U.S. Application Data

(63) Continuation of application No. 14/884,491, filed on Oct. 15, 2015, now Pat. No. 10,456,159.

(60) Provisional application No. 62/065,501, filed on Oct. 17, 2014.

(51) Int. Cl.
| | |
|---|---|
| *A61B 17/3207* | (2006.01) |
| *A61B 17/221* | (2006.01) |
| *A61B 17/22* | (2006.01) |
| *A61F 2/01* | (2006.01) |

(52) U.S. Cl.
CPC .... *A61B 17/320725* (2013.01); *A61B 17/221* (2013.01); *A61B 17/320758* (2013.01); *A61B 2017/2212* (2013.01); *A61B 2017/22079* (2013.01); *A61B 2017/320716* (2013.01); *A61B 2017/320733* (2013.01); *A61F 2002/018* (2013.01)

(58) Field of Classification Search
None
See application file for complete search history.

(56) References Cited

U.S. PATENT DOCUMENTS

| | | | | |
|---|---|---|---|---|
| 6,238,412 B1* | 5/2001 | Dubrul | ................... | A61B 17/22 606/108 |
| 6,660,021 B1* | 12/2003 | Palmer | ................... | A61F 2/013 606/200 |
| 6,695,813 B1* | 2/2004 | Boyle | ...................... | A61F 2/01 604/106 |
| 2001/0031981 A1* | 10/2001 | Evans | .................. | A61B 17/221 606/200 |
| 2004/0026942 A1* | 2/2004 | Kessler | ................ | A61B 17/221 294/100 |

(Continued)

*Primary Examiner* — Shaun L David
(74) *Attorney, Agent, or Firm* — YOUNG LAW FIRM, P.C.

(57) ABSTRACT

A device for intra-vascular embolic-thrombolic protection, as well as embolectomy/thrombectomy and atherectomy interventional procedures and methods. At least a portion of the working end of the device may be formed monolithically from a single hypodermic tube, or may be formed of monolithic inner and outer tubes with fixed or movable guide wire elements and imaging modalities. The device may comprise structures enabling coring, expansion within a vascular structure and vascular wall shaving, as well as filtration, stabilization and capturing of thrombotic or embolitic material during an intervention procedure.

19 Claims, 7 Drawing Sheets

(56) References Cited

U.S. PATENT DOCUMENTS

| | | | | |
|---|---|---|---|---|
| 2004/0236368 | A1* | 11/2004 | McGuckin, Jr. | A61F 2/011 606/200 |
| 2004/0260333 | A1* | 12/2004 | Dubrul | A61M 25/0119 606/200 |
| 2008/0208230 | A1* | 8/2008 | Chin | A61B 17/32002 606/167 |
| 2009/0299393 | A1* | 12/2009 | Martin | A61B 17/221 606/159 |
| 2011/0034986 | A1* | 2/2011 | Chou | A61M 27/002 623/1.11 |
| 2011/0184447 | A1* | 7/2011 | Leibowitz | A61B 17/320016 606/170 |
| 2011/0288572 | A1* | 11/2011 | Martin | A61B 17/221 606/159 |
| 2013/0317409 | A1* | 11/2013 | Cully | A61B 17/12045 604/6.09 |
| 2013/0317589 | A1* | 11/2013 | Martin | A61B 17/3207 623/1.2 |
| 2017/0020540 | A1* | 1/2017 | Chou | A61M 25/04 |

* cited by examiner

THROMBO-EMBOLIC PROTECTION AND EMBOLECTOMY/THROMBECTOMY DEVICES AND METHODS

BACKGROUND

Embodiments relate to medical devices and methods. More particularly, embodiments relate to thrombo-embolic protection and embolectomy/thrombectomy devices and methods. Additionally, embodiments relate to atherectomy devices and methods.

SUMMARY

Embodiments are drawn to medical devices and methods that may be used for, for example, intra-vascular thrombo-embolic protection and embolectomy/thrombectomy and atherectomy procedures. According to one embodiment, an intra-vascular interventional device may be configured to prevent and/or remove clots, plaque or thrombus materials, in solid or semi-solid form during a single insertion through the skin (percutaneous intra-vascular procedure), or directly into a vessel via open surgical procedures into any vascularized area of the body. Embodiments may comprise structures and functionality for different phases of a multi-phase intra-vascular intervention procedure, which may be performed by hand using any of a variety of imaging technologies, such as Optical Coherence Tomography (OCT) or ultrasound or others, or by attachment to a stereotactic table stage or Magnetic Resonance Imaging (MRI) stage. Embodiments may also be inserted through the central lumen of another compatible intra-vascular interventional device. Embodiments of an intra-vascular thrombo-embolic intervention device, along with associated related subcomponents described herein, may be configured to trap and/or retrieve solid or semi-solid, contiguous and/or fragmented materials and tissues as well as liquid and near liquid state tissues and materials for analysis, diagnosis and further treatment. Embodiments may be configured to be portable, disposable or reusable and may be, for example, electrically-, mechanically-, hydraulically-, pneumatically- and/or manually-powered and operated.

DETAILED DESCRIPTION

Reference will now be made in detail to the construction and operation of implementations of the embodiments illustrated in the accompanying drawings. The following description is only exemplary of the embodiments described and shown herein. The embodiments, therefore, are not limited to these implementations, but may be realized by other implementations.

According to embodiments, a device for thrombo-embolic and mixed thrombotic lesion interventional procedures may be formed of one or more co-axially located stainless steel (for example) hypodermic tubes (hypo tubes) that are configured with (e.g., laser) cuts at its working end (the work element of the device, disposed at or near a distal end) to allow the work element to assume various forms, shapes and configurations at various stages of an interventional procedure, according to embodiments. The tube or tubes of the device may be rigid over portions of the device. According to other embodiments, the tube(s) may be flexible over the entire length or one or more portions thereof. Embodiments may comprise or be formed of materials other than stainless steel such as, for example, plastics or other suitable materials, which may incorporate the features of the work elements described herein.

Figure 1A:
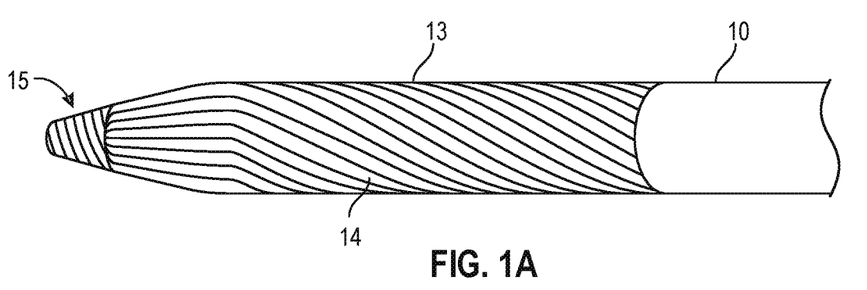
FIGS. 1A, 1B, 1C, and 1D are perspective side views of components of a thrombo-embolic interventional device, according to embodiments.

FIGS. 1A, 1B, 1C, and 1D are perspective side views of components of a device, according to embodiments. The device if FIGS. 1A-1D may be configured to thrombo-embolitic interventional procedures, according to one embodiment. As shown, FIG. 1A is a side view of a work element 13 of a device 10 in a resting state, configured as an outer component 14 with nosecone 15, which also acts as a twisting brake. The outer component may be configured with straight and succeeding spiral cuts in a standard hypo tube. These laser cuts, according to one embodiment, may terminate at the proximal end of the work element (the distal portion of a device 10), leaving a tube that may run proximally to a handle 12 (not shown in this view).

A nosecone 15, as represented with angled lines that may represent sharp blade elements, may be rotated with the remainder of device 10 in low profile state according to an embodiment, in order to advance through thrombo-embolic or mixed (plaque/thrombo-embolic type) lesions, to provide a channel and to enable downstream embolic protection once beyond the obstruction.

Figure 1B:
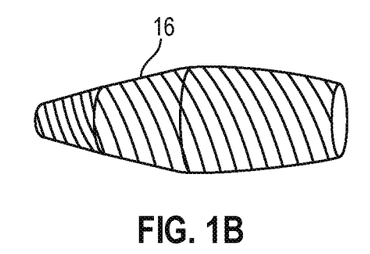

FIG. 1B shows a flexible component 16 of a work element 13 of a device 10, according to one embodiment. As shown, flexible component 16 may be formed of a stretchy, partially porous material that may become more porous when it is stretched as a result of activation of the work element 13. The flexible component 16 may be slipped over a nose cone 15 of work element 13, and may serve as a particle trap for embolic materials that may be released by another intra-vascular interventional device, with which device 10 may be used in conjunction, according to one method. Flexible component 16 may also serve as an elastic component to cause the nosecone 15 of work element 13 to return to its original configuration of a smaller diameter, or resting position, as shown above in FIG. 1A. Flexible component 16 may be used to cover an embodiment of a nosecone 15 comprising cutting elements that may be shielded until needed for boring through vascular obstructive material. Flexible component 16 may also be or comprise an inflatable balloon that may be even lower profile than the embodiment shown herein. Such a balloon may be advanced ahead of (distal to or downstream from) device 10 to provide an even more distal protective component. The flexible component 16 may be inverted/everted by the advancement of device 10 into the proximal end of flexible component 16 to enable smooth passage of device 10 and may also, by the same action, trap any embolic material between component 16 and device 10, according to an embodiment. According to one embodiment, device 10 may be configured to slide through the center of flexible component 16 which, when inflated, may assume the shape of an elongated-side-wall, hollow tube, with an inflated collar configuration, which may be further configured to have an open center that is sufficiently large to enable device 10 to slide there-through, according to another embodiment. Component 16 may be configured as an elongated balloon having a sufficiently low profile in its deflated, unexpanded state to enable device 10 to slide over its outer circumference, once any thrombo-embolic or mixed material (complex obstruction containing both thrombo-embolic and plaque-type components) if in a complex lesion, is removed by device 10, to thereby render the vessel safe enough to allow deflation of component 16 according to an embodiment.

Figure 1C:
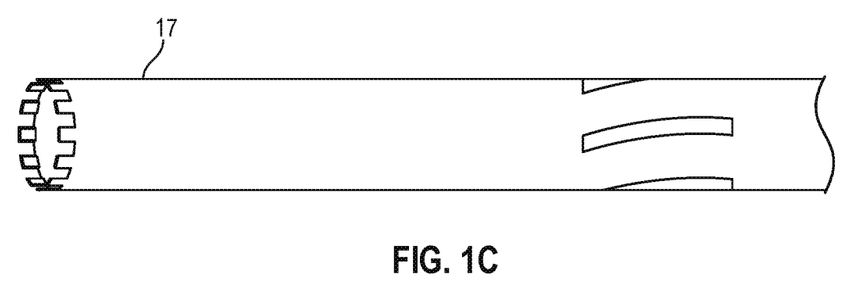

FIG. 1C shows a side view of an inner tube member 17 of a work element 13. Inner tube member 17 may be configured to spread the straight and spiral portions of an outer tube 14 when it comes into contact and interlocks with nosecone 15. According to one embodiment, such an inner tube member 17 may be configured with castellations or other configurations at its distal-most free end that, when pressed against the inside of nosecone 15 and twisted, may act upon it to correspondingly twist nosecone 15 of outer tube 14, In turn, such twisting of nosecone 15 may unwind the spiral cuts of outer tube 14, forcing them to resiliently expand in overall diameter inside a vascular structure as they at least partially untwist. Also shown in this figure are openings "o" that are configured to allow liquids to pass, but that are sized such that any solid materials or particles will tend to pass by such openings to be trapped in the nosecone 15 of FIG. 1A. Inner tube member 17 may be configured as a vacuum conduit, its castellation configuration serving to maintain a small gap through which particulate and gelled matter may be suctioned for removal, according to an embodiment.

Figure 1D:
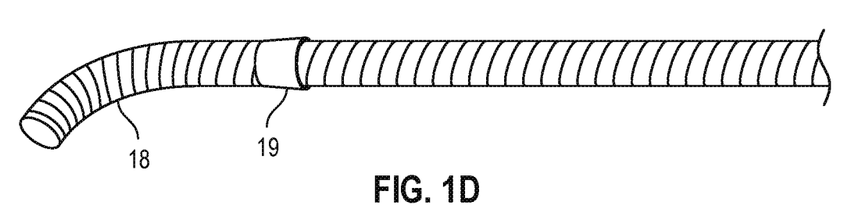

FIG. 1D shows a side view of a movable guide wire or catheter 18 of work element 13, according to one embodiment. According to embodiments, such a guide wire component 18 may be sufficiently small, for example from 0.009" to 0.014", to be passed through a very small inner lumen of device 10 such that device 10 may be easily passed through a 4 French or 5 French guiding catheter. Such a guide wire 18 may be shapeable and/or steerable at its distal end and may also be configured with a bushing element 19 that may bear against the distal rim of nosecone 15, such as that of FIG. 1A above, in order to serve as a bearing surface to spread the straight and spiral cuts of an outer tube 14. Bushing element 19 may be used to vary the slit-like opening between itself and the distal nosecone of device 10 or flexible component 16. When used in this manner, when vacuum is applied in the center of device 10 in a configuration in which the inner tube element is used as a conduit for vacuum, bushing element 19 may be movable to vary the size of the slit-like openings to optimize vacuum and also to control the size of particulate matter being suctioned in such slit-like openings, according to an embodiment. According to one embodiment, guide wire 18 may also be configured to comprise opening blocker elements that may, when aligned, block the openings in inner tube 17 designated "o" in FIG. 1C and that may, when twisted out of alignment, open the openings "o" in inner tube 17.

Figure 2:
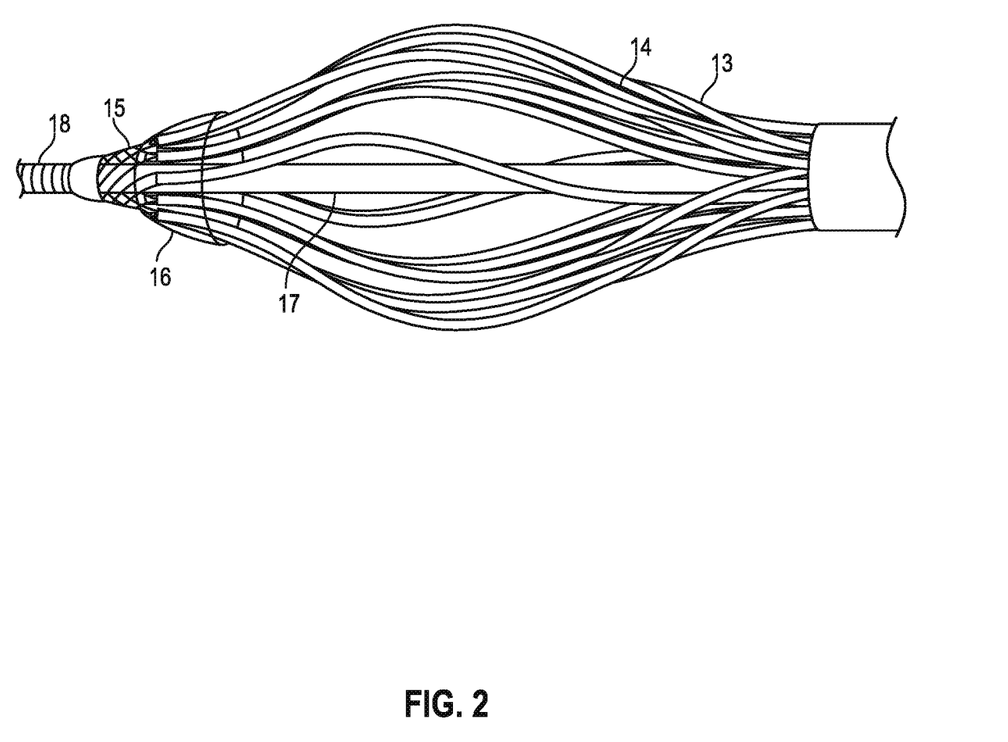
FIG. 2 show details of the work element of a thrombo-embolic interventional device of FIGS. 1A-1D in a vascular structure, according to one embodiment.

FIG. 2 shows details of a work element 13 comprising the components shown in FIGS. 1A, 1B, 1C, and 1D, according to one embodiment. The work element 13 may be, according to one embodiment, a monolithic structure comprising a plurality of twisted slats or ribbons formed from a single stainless steel hypo-tube. The slats or ribbons may be formed from the single hypo tube by laser cuts such as the kerfs shown in the outer tube 14. A second inner tube 17 may be provided to serve as an actuating component to expand (by at least partial untwisting, for example) the slats or ribbons formed by the laser kerfs. Work element 13 may thus also comprise a vascular expanding device that does not require a balloon element, according to one embodiment. According to another embodiment, the work element 13 may be deployed to augment the outwardly-directed pressures of an expanded balloon element against the walls of a vascular conduit, to aid in the beneficial expansion thereof. Work element 13 may be further configured to comprise sharp struts that, under pressure from its own expansion or together with additional balloon expansion forces, may be used to alter the restriction strength of the obstructive material, to render it easier to expand by expansion forces. Such sharp struts may, in operation, at least superficially cut the obstructive material, rendering it more susceptible to yield under pressure, in a similar manner that glass is more easily and controllably broken once even a superficial scoring line has been made therein. Work element 13 may be rotated, oscillated and/or translated to enable a fully contacting (i. e., all around the inside diameter of a lesion) sabre-like, sawing or draw-knife-type cutting-scoring action to raise the level of cutting efficiency applied to a lesion according to an embodiment. Work element 13 may thus serve as an atherectomy device, since once obstructive material has been sliced away from the vascular wall, the material will necessarily be located inside device 10 and may thereafter be subjected to collection with vacuum, simple trapping for later removal or other forms of active tissue transport out of the vascular space, in the proximal direction within device 10, according to embodiments. Outer strut portions of work element 13, once expanded, may be detached and left in situ to serve as a temporary removable or absorbable stent, or it may serve as a permanently-implanted vascular scaffold (stent).

An expanded work element 13, in one embodiment, may be used as a temporary stent without being detached from its proximal portion, thereby allowing or maintaining blood flow as an intermediate, time gaining step between other vascular intervention procedures. Indeed, such use as a temporary stent may be advantageous to use before, during or after other interventional procedures to allow other supporting vascular structures to be worked on during a complex interventional procedure. According to one embodiment, when the device is used as an atherectomy device, it may be advantageously advanced into a nearly occluded vascular structure. Several passes may be made through a restricted segment of the vascular structure, with each pass being made using a slightly greater outside diameter of the work element, which may be adjustable. In so doing, a smooth opening through the vasculature may be gradually and gently enlarged. Additionally, according to one embodiment, if a graft is to be placed in the smooth bored inner surface of a vascular structure, the graft may be gently wrapped around a work element that is in its most relaxed, or smallest diameter, configuration. The work element with wrapped graft may be advanced to the graft site, expanded to place the graft concentrically against the inner smooth wall of the vascular structure. The so-placed graft may be held in place until the distal and proximal edges of the graft are fixed in place. Advantageously, use of a work element as a graft placement, expansion and anchoring device allows blood flow through the expanded work element spirals during placement of the graft. This also allows the graft to be fixed in place by other interventional devices and modalities, after which the work element may be withdrawn from the body. According to one embodiment, anchoring elements may be provided at the proximal and/or distal ends of the stent and/or graft placing work element. These anchoring elements may comprise, for example, barbs, hooks and/or other shapes that may be twisted or pressed into place using one of the embodiments of the work element shown and described herein.

As shown in this figure, the castellations of the inner tube 17, as shown in FIG. 1C above, may engage the kerfs of the outer tube 14 at the distal end, and a torque moment applied on the inner tube 17 while holding the outer tube 14 stationary (non- or differentially revolving with relation to inner tube 17) will thus deploy the slats of the outer tube 14 and cause the effective diameter of the work element 13 to expand. One of the advantages of the use of castellations on the inner tube to positively engage the distal end of the outer tube for actuation is that, once an inner tube 17 has performed its function, it may be withdrawn proximally to provide more internal space within the outer tube 14 for clot or debris materials (resulting from an interventional procedure) to fill in thus-enlarged space to make the device easier to retrieve once that internal space is filled.

According to one embodiment, the inner tube 17 may not be castellated at its distal end, but may be laser welded, for example, at its distal end to the outer tube 14. FIG. 2 shows such a work element 13 in a vascular structure with a side branch denoted "SB". It should be noted that with such a placement, the kerfs that are widened as a result of the twisting moment imparted to the outer tube 14 by the inner tube 17 may allow fluid passage, shown as "f" in this figure, from the main vessel to the side branch and downstream along the main branch, but may trap and prevent at least some embolic matter from flowing downstream, assuming that blood flow is from right to left and as implied by the shape and angle of the side branch in this figure. Such embolic materials, shown as particles "p" in this figure, may continue to flow downstream within the main channel of the main blood vessel to be trapped in the nosecone 15 with its flexible outer coating 16.

According to embodiments, various longitudinal sections of the outer tube slats formed by laser kerfs may be of different hardness or flexibility as a result of, for example, heat treatment or shape configuration, as examples of such treatments, to allow a variety of shapes to be formed by the deployed slats of the outer tube 14. As such, such shapes may serve to impart different functionalities to the work element, which may include serving as an atherectomy work element to shave plaque or other materials from a vascular structure's internal walls and capture such materials in a deployed flexible element 16, thus preventing their escape downstream. In such an embodiment, the laser kerfs may be formed as secant cuts, rather than radius cuts in the outer tube to impart a sharp leading edge to each slat. In such an embodiment, it may be advantageous to correctly size the outer diameter of the deployed slats of the outer tube of the work element, in order to determine how aggressively plaque may be shaved from the inner walls of a vascular structure.

According to further embodiments, an inner tube 17 or outer tube 14 may be configured for aspiration from its or their central lumens to remove embolic material during an interventional procedure. Additionally, work element 13 may be configured to contain or enable passage of any of a number of compatible imaging modalities, such as a guide wire with fiber optic camera, ultra sound imagery capturing or OCT scanning, for example.

Figure 3:
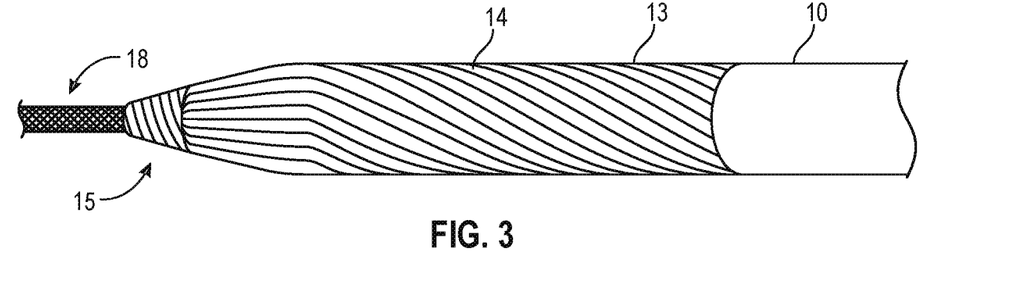
FIG. 3 is a side view of the work element of the thrombo-embolic interventional device of FIGS. 1A-1D and 2 in a relaxed state, according to one embodiment.

FIG. 3 is a side view of the work element of the thrombo-embolic interventional device of FIGS. 1A-1D and 2 in a relaxed, resting or relaxed (e.g., un-expanded) state, according to one embodiment. In this view, outer tube 14 is in its most axially elongated and minimum diameter configuration. Elements such as the nosecone 15, fixed or removable guide wire 18 and a stiff or flexible body portion connected to the work element 13 are also shown. In this configuration, device 10 may be introduced into a vascular structure and induced to cross over an area of thrombus, embolus or thrombotic occlusion. As indicated in this figure, different longitudinal areas or sections of the work element 13 may be configured to be straight or spiral-cut, and may include shapes or hardness features that may influence the three-dimensional shape of the work element 13 in its deployed configuration, according to embodiments. Additionally, a flexible membrane element 16, such as shown in FIG. 1B, or a perforated outer coating element may be incorporated into the work element 13.

Figure 4:
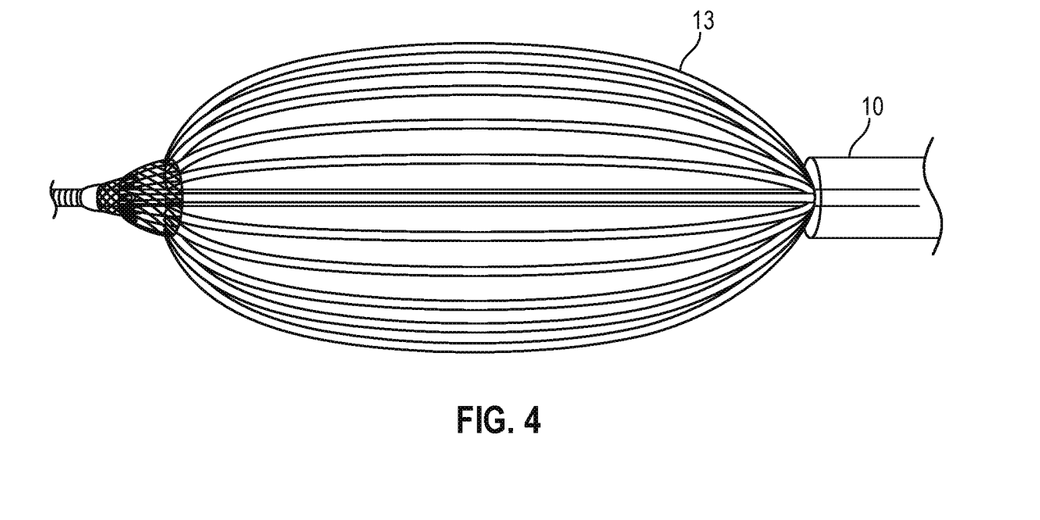
FIG. 4 is a side view of the work element of the thrombo-embolic interventional device of FIGS. 1A-1D, 2 and 3 in an unwound state, according to one embodiment.

FIG. 4 is a side view of the work element of the thrombo-embolic interventional device of FIGS. 1A-1D, 2 and 3 in an unwound state, according to one embodiment. As shown, the device 10 of FIG. 3 is shown in a configuration in which the work element 13, including the outer tube 14 and other elements previously described above, are in a maximum unconstrained configuration, i.e., unconstrained by a vascular wall in which it may be placed. If placed in a vascular structure, the maximum diameter of the work element 13 may be comparatively less than the maximum unconstrained diameter and may be carefully tuned to allow the laterally-expanded slats of the outer tube to shave plaque or other material from the walls of such a vascular structure, while enabling blood flow and the capturing of debris to occur, according to embodiments.

Figure 5:
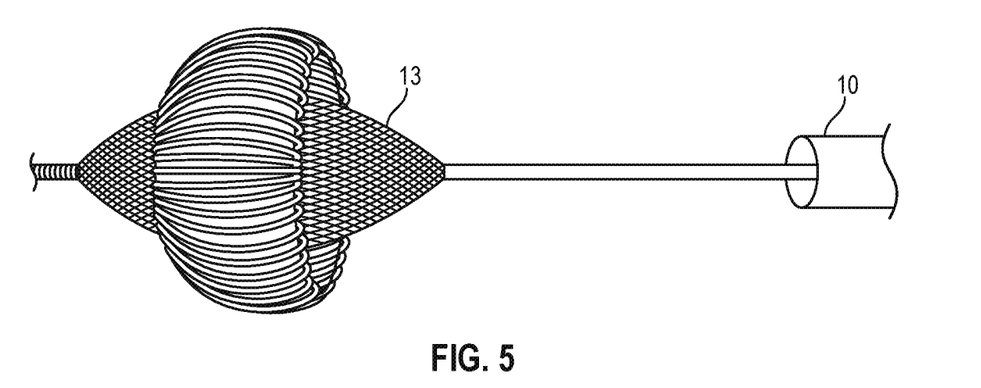
FIG. 5 shows the work element of the thrombo-embolic interventional device of FIGS. 1A-1D, 2, 3 and 4 in an inverted step, according to one embodiment.

FIG. 5 shows the work element of the thrombo-embolic interventional device of FIGS. 1A-1D, 2, 3 and 4 in an inverted configuration, having passed through a thrombus in a vascular structure, according to one embodiment. In this embodiment, once deployed distally to a thrombus, the work element is first expanded in the manners described above. Thereafter, an inner tubular element may be advanced forward (i. e., in the distal direction), expanding the struts thereof until they buckle and cause inversion of the proximal portion of spiral strut elements which, according to one embodiment, may be separable from the outer tube. The entire device may be retracted proximally during this maneuver. This proximal retraction creates a surrounding, capturing motion as the more distal strut elements enable the outer rim, where flexible struts that are progressively inverted, to meet up with stiff, membrane covered, more firmly radially outwardly disposed portions of themselves.

The distal portions of the strut elements may be "stiffer" and more prone to remain extended that the proximal portions of the strut elements. The distal portion of the strut elements may additionally be covered with an ultrathin membrane. This causes inversion all the way to the point where they end in the non-kerfed proximal portion of the main outer tube. At this point they, being shorter in length than the more stiff distal portions of themselves, while continuing to be forced distally by the proximal disc (of smaller diameter than the main tube) or alternatively by the main tube, non-kerfed section, act as bowstringing tethers to help bring the proximal-most sections of the stiffer portions of the strut inwards at their most proximal point (where stiff meets less stiff sections). This motion may be accompanied and augmented by a re-twisting of the strut elements to further squeeze down on and more firmly capture thrombotic and mixed debris. In this manner, any debris thus internalized by these mechanisms and elements may be firmly, actively and securely captured. The device 10 may be introduced into a vascular structure from either an upstream or downstream position relative to the thrombus to be passed.

Figure 6:
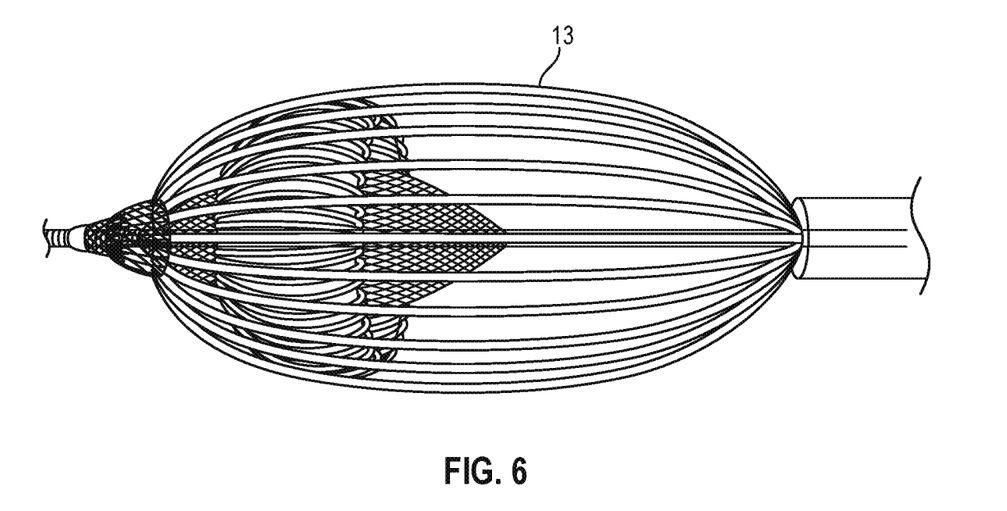
FIG. 6 shows perspective views of superposed pre- and post-inversion configurations of the work element of the thrombo-embolic interventional device of FIGS. 1A-1D, 2, 3, 4 and 5, according to one embodiment.

FIG. 6 shows a perspective view of superposed pre- and post-inversion configurations of the work element 13 of the thrombo-embolic interventional device of FIGS. 1A-1D, 2, 3, 4 and 5, according to one embodiment. It is to be understood that the device 10 does not assume the pre- and post-inversion configurations shown in FIG. 6 at the same time, as both configurations are shown for purposes of explanation only. In this figure, the laterally expanded, but not yet forwardly deployed slats of an outer tube are shown superposed over the configuration discussed relative to FIG. 5 above. In this latter configuration, the inner tube may be configured with a collar mechanism to capture the proximal portion of the outer tube slats, and thus drive them forward after having imparted a twisting rotational force to the outer tube slats to deploy them laterally. Such a combined twisting force to deploy laterally, and then distal axial force alone or in combination with further twisting to reach a second configuration, such as in FIG. 5 above, allow for an efficient and positive closure and constitute an effective entrapment mechanism to prevent embolic material from flushing downstream from an interventional site, according to one embodiment. As discussed above, some or all of the struts of the work element may be sharpened along an edge thereof such that, in the fully expanded state, work element 13 may be configured, deployed and used as an expandable, circular atherectomy device to clear adherent obstructive materials from vascular walls. Such a device may simultaneously collect such cut obstructive materials within the confines of work element 13 of device, 10 according to an embodiment.

Similarly, once configured as in FIG. 5, work element 13 may have only portions of its sharpened strut elements near the extreme flex-points that form the circumferential rim, which rim is firmly pressed against the lesions lining the vascular walls. In this embodiment, rotation, oscillations and proximal translation or a combination of strut element and the rim formed by the extreme flex points thereof may serve to sever the obstructing lesions from vascular walls. The circumferential rim of sharpened and flexed struts or slats may, in this manner, form the cutting edge that cuts and severs the obstructing lesions. According to one embodiment the cut and severed obstructing material may then be collected in, for example, the manner previously described. According to embodiments and as shown in FIG. 6, work element 13 may be configured to be attached to a main outer tube 14 of device 10 at either of its ends. In this manner, work element may be used in a vessel and advanced within the vasculature in an orientation in which the flow is antegrade (i. e., approaching an arterial conduit or vein graft from upstream side) or retrograde i. e., approaching either of those structures from downstream side and vice versa in direction for in-situ venous conduits).

According to embodiments, the work elements 13 may be constructed of or comprise shape memory materials and configured such that, exposure to body temperatures causes the work element to expand under the forces contained within the materials, augmented or combined with geometrical cuts configured to optimize and refine such forces. According to one embodiment, other portions of work element 13 may also aid expansion of the work element 13. In another embodiment, such expansion may be configured to allow or cause detachment of all or certain portions of work element 13 such that these elements may be left in-situ to serve as temporary or permanent vascular scaffolding (stent). As temporary scaffolding, these elements may be configured to be retrievable by reversing the process (i.e., subjecting the materials of work element 13 left in-situ to higher or lower temperatures or another form of energy) and re-attaching work element 13 or portions thereof, in situ, to a retrieval device 10, according to embodiments.

Figure 7:
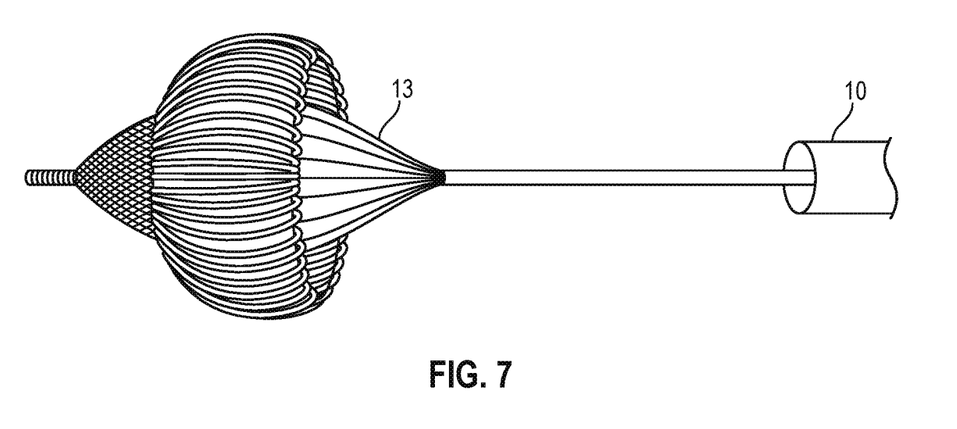
FIG. 7 shows a side perspective view of a work element of a thrombo-embolic interventional device of FIGS. 1A-1D, 2, 3, 4, 5 and 6, according to one embodiment.

FIG. 7 shows a side perspective view of the work element of the thrombo-embolic interventional device of FIGS. 1A-1D, 2, 3, 4, 5 and 6, according to one embodiment. In this view, the slats of the outer tube have been deployed forward are about halfway towards full expansion of the work element 13 within a vascular structure. This illustrates that the ultimate outer diameter of the work element may be adapted to the morphology or diameter of the vascular structure within which it may be introduced and deployed.

Figure 8:
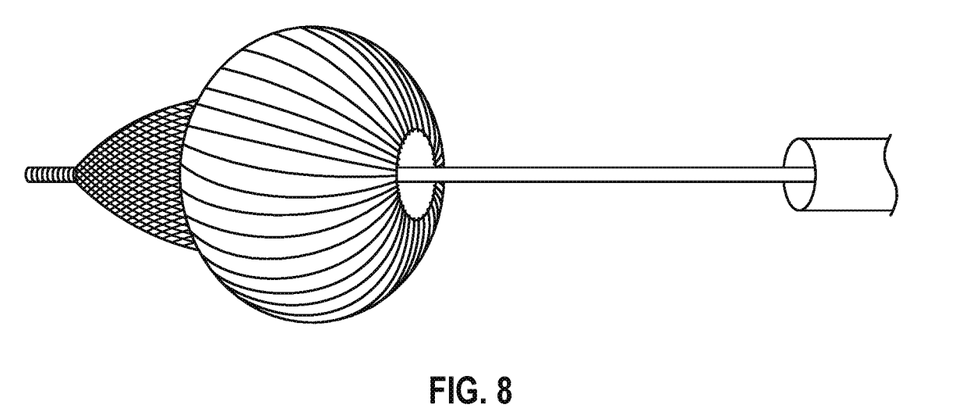
FIG. 8 shows a side view of the work element of the thrombo-embolic interventional device of FIGS. 1A-1D, 2, 3, 4, 5, 6 and 7, according to a method according to one embodiment.

FIG. 8 shows a side view of the work element of the thrombo-embolic interventional device of FIGS. 1A-1D, 2, 3, 4, 5, 6 and 7, according to one embodiment. This view shows a later in time configuration of the device in operation, as compared with the views shown in FIGS. 1A-1D, 2, 3, 4, 5, 6 and 7. Indeed, in FIG. 8, the work element is shown in a completely deployed or closed configuration with a maximum outside diameter, and with a double basket effect as a result of the inversion of a portion of the outer tube slats within a more distal portion. Such a configuration may allow for complete diametrical sealing of the inner lumen of a blood vessel, while still allowing blood flow and simultaneous capture of very small particulates such as embolic materials. Such a work element in this deployed shape may also be withdrawn from a blood vessel without risk to sensitive vascular wall structures, while retaining captured materials in its double basket shape.

Figure 9A:
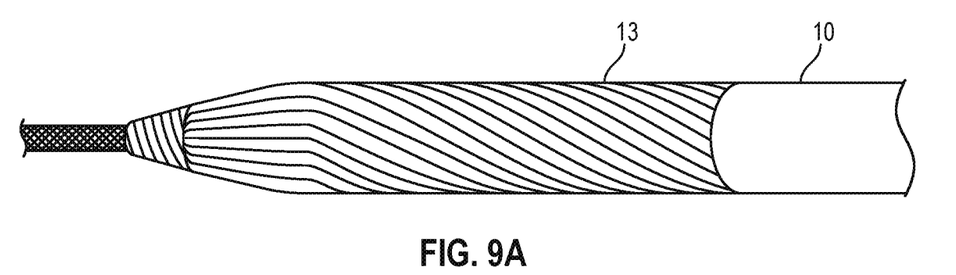
FIGS. 9A and 9B show two states of the work element of the thrombo-embolic interventional device of FIGS. 1A-1D, 2, 3, 4, 5, 6, 7 and 8, according to one embodiment.
Figure 9B:
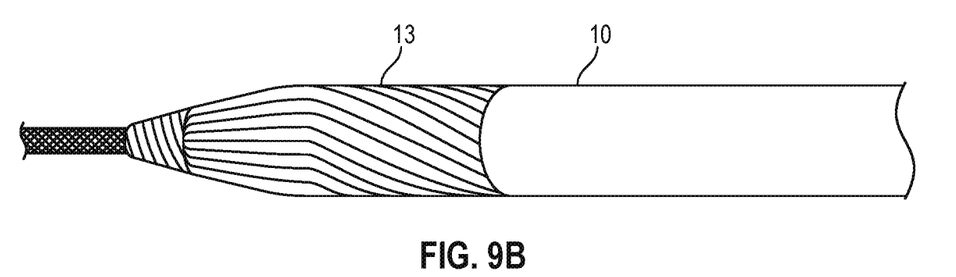

FIGS. 9A and 9B show two states or configurations of the work element 13 of the thrombo-embolic interventional device 10 of FIGS. 1A-1D, 2, 3, 4, 5, 6, 7 and 8, according to one embodiment. FIG. 9A shows the work element in its initial state, as compared to the post-interventional state of the device shown in FIG. 9B. In FIG. 9A, rotational torque force has not been applied to the outer tube slats, which remain tightly closed for ease of penetration of a thrombus, for example. In this state, the work element has a low profile suitable for insertion in small diameter openings and structures. FIG. 9B shows the device of FIG. 9A in a post interventional state, in which a thrombus has been captured within the now-closed outer tube. As shown, the closed outer tube may be configured to wrap, envelop and encapsulate the cut thrombus material within in its central lumen. In this configuration, the work element of the device 10 is ready to be withdrawn from the body, together with the cut and captured material according to one embodiment, the device 10 may be implemented in a hand-held configuration comprising an ergonomically comfortable and secure handle at its proximal end. Work element 13 may extend from the handle to enable the device 10 to be easily grasped, directed and operated with one hand. Other embodiments may be readily adapted to fit onto any number of guiding devices such as a stereotactic imaging stage or other guidance modality such as MRI. As shown, one embodiment of the device 10 may comprise one or more sharp elements (herein, alternatively and collectively referred to as "work element 13") projecting forward distally from the handle for the purpose of forward penetration, coring, shaving and capturing of cored or shaved materials in an interventional procedure. As shown, one embodiment may comprise a work element 13 that may comprise one or more sharp cutting tip or side blades to penetrate to the target site of the intended intervention. The entire device 10 may be configured to be disposable or may be configured to be reusable in whole or in part.

A device 10, as disclosed herein, is an effective, low profile instrument that does not require a constraining delivery device and that also incorporate a self-sealing retrieval system that does not necessarily require a separate capture tube. Such a device, according to embodiments, may be configured for at least three main purposes, namely 1) distal protection filtering, with built in distal guide-wire, imaging and medication delivery conduit(s). (embolic protection device), 2) embolectomy/thrombectomy retrieval, and 3) temporary vessel patency maintenance. Additionally, one embodiment may be configured as a distal-to-proximal "crawling capture" device, which is also active in expansion, crawling function and capture "sealing" function. According to embodiments, devices 10 may make use of mechanical, active expansion coupled with passive/active closure, relying on untwisting of spirally disposed, living hinge incorporating elements, alone or in combination with compression/extension elements to enhance expansion, contraction and trapping/sealing of debris, whether capture in-situ (thrombectomy/embolectomy) is the therapy or prevention of distal embolization or clot propagation is the goal of the interventional use of a device 10. Such devices may comprise membranous elements, such as shown above in FIG. 1B, whose pore sizes can be controlled based on expansion/relaxation of the stretching of strut elements. The devices 10 may also enable central, filtered and unfiltered but particulate-diverted, flows through and beyond the devices to nourish distal vasculature watershed areas downstream.

According to embodiments, the device 10 may comprise a main tubular element into which are formed a pattern of, for example, laser kerfs that begin as straight cuts (generally parallel with the long axis of the tube) distally, to aid radial expansion when the cuts portion of the tube is compressed distal/proximal in the axial plane. These cuts may then be more spirally disposed proximally to maximize their radial expansion during "unwinding" of the helix by a combination of resistance to twisting (the main tube) forces imposed by an inner tubular element. Both inner tubular element and outer main tube may proceed proximally all the way to a handle element 12 that enables controlling the twist and compression functions at the distal working end of the device. The axial compression (result of which augments radial expansion of the twisting "unwinding" forces) may be actuated by a combination of resistance to forward travel of the distal nosecone of the device by the guide-wire element (in a variant where the inner tubular element is removable), or the inner tubular element (in the case of the inner tubular element being non-removable from the outer main tube, and essentially fixed to the nose cone), while the main tube is forced forward by the inner tube element. This simultaneously opens the flow channels in the inner tubular element. Alternatively, the proximal tube may be both twisted and forced forwards by the portion of the main tube that is proximal to the spiral kerf section, in which only one of the inner tubular element or the guide-wire element is needed in that case, assuming the guide-wire element is strong enough to prevent twisting of the nose cone), according to various embodiments. As thrombotic or mixed material debris begins to fill the distal nose cone area, prevented as it is from traveling distally by the membranous portion covering the distal roughly half of the kerf section of the main tube, the debris (cut material) accumulation creates a relatively lower pressure area distal to the flow slots that help prevent debris from entering these channels. Additionally, the streamlined nature of the slots works to exclude all but the smallest and lowest inertia debris, while a shield or flow chamber may also be incorporated for certain clinical indications. The channel openings may be specifically configured to permit only high speed jets of flow, which generally dissolves any partially clotted fluids. In certain clinical indications or milieus such as acute myocardial infarction, pulmonary embolization and other acute situations, structures may be provided to prevent the inclusion of particulate material. Such structures may exclude particulates through predetermined fenestration geometry alone or in combination with active twisting of the inner tubular element. Fluids to dissolve the clot that pass by centrifugal forces (occasioned by rotating at least the work element) through the fenestrations are stirred to dissolve clot while excluding particulates. Assuming the rotational speeds may be optimized for imaging modalities, such imaging modalities may be included, for purposes of up close imaging of thrombotic elements as well as their excision and transport during use of these devices. According to further embodiments, a motorized spinning guidewire may be provided and used in conjunction with the present devices 10 to a-traumatically stir downstream to keep flows active and the clotting elements dissolved. According to a further embodiment, the entire outer main tube may be gently spun. The spiral slats of the spinning outer main tube, in its expanded configuration, may be caused to a-traumatically sweep the walls of an affected blood vessel. Dislodged or cut material may then be collected by the geometry of the most radially pressing elements located further upstream. If needed, vacuum may be provided, utilizing the inner tubular element conduit, which can be switched back to distal flow provision (with the source of vacuum unhooked or otherwise deactivated) once the bulk of the thrombotic or mixed debris is removed.

According to methods, during interventional procedures for cases such as those of carotid angioplasty, stenting and endarterectomies, protection against distal (into the brain vasculature) embolization is vital. In these cases, the primary material is friable, particulate plaque that usually includes some thrombotic debris, although usually, it is fairly commonly organized thrombus, rather than active. If the patient has recently had a transient ischemic attack (TIA) or reversible ischemic neurologic deficit (RIND, which is usually longer and deeper than a TIA) the thrombus has already given rise to emboli. In any case, such material, once released, is capable of causing additional thrombotic events in the area local to which it embolizes. These same principles apply to peripheral vascular interventions in other areas of the body, such as upper and lower extremities and renal arteries, among others. In acute ischemic events, for example, acute myocardial infarction, pulmonary infarctions and peripheral arterial acute occlusions, there are active thrombotic events and these include distal embolization events. In such cases, there are two vital needs, the first being to retrieve any active thrombus and the second being to administer pharmacological agents to prevent further thrombosis and clot propagation while also minimizing the chance of (further) embolization. At the same time, any thrombi or emboli already too far distally located for practical retrieval can be dissolved by so called "clot-buster" pharmacologic regimens. The key is to retrieve and remove thrombi and emboli from the major vessels since they serve the largest watershed areas and thus create the greatest and most permanent tissue damage. Additionally, the more thrombotic material removed, the less the clotting system is activated by free-floating elements. The lower the clot burden, the lower is the required dosage of "clot busting" medications. Another strong indication for thrombus removal and embolus protection is in the attempted salvaging of old vein graft bypass conduits, which, when they become ectatic, are notoriously filled with thrombus in various states of organization. These are large bulky thrombi that are likewise notoriously prone to embolization once disturbed by interventional procedures. Regardless of the intervention, these require thrombus removal and protection against distal embolization. There are many other examples of indications such as dialysis grafts among others, but the examples cited herein most closely represent the variety of types of vascular indications for removal (thrombectomy/embolectomy) and protection (embolic protection devices) against ischemia from vascular occlusion due to thrombi and emboli before, during and after an interventional procedure.

Figure 10:
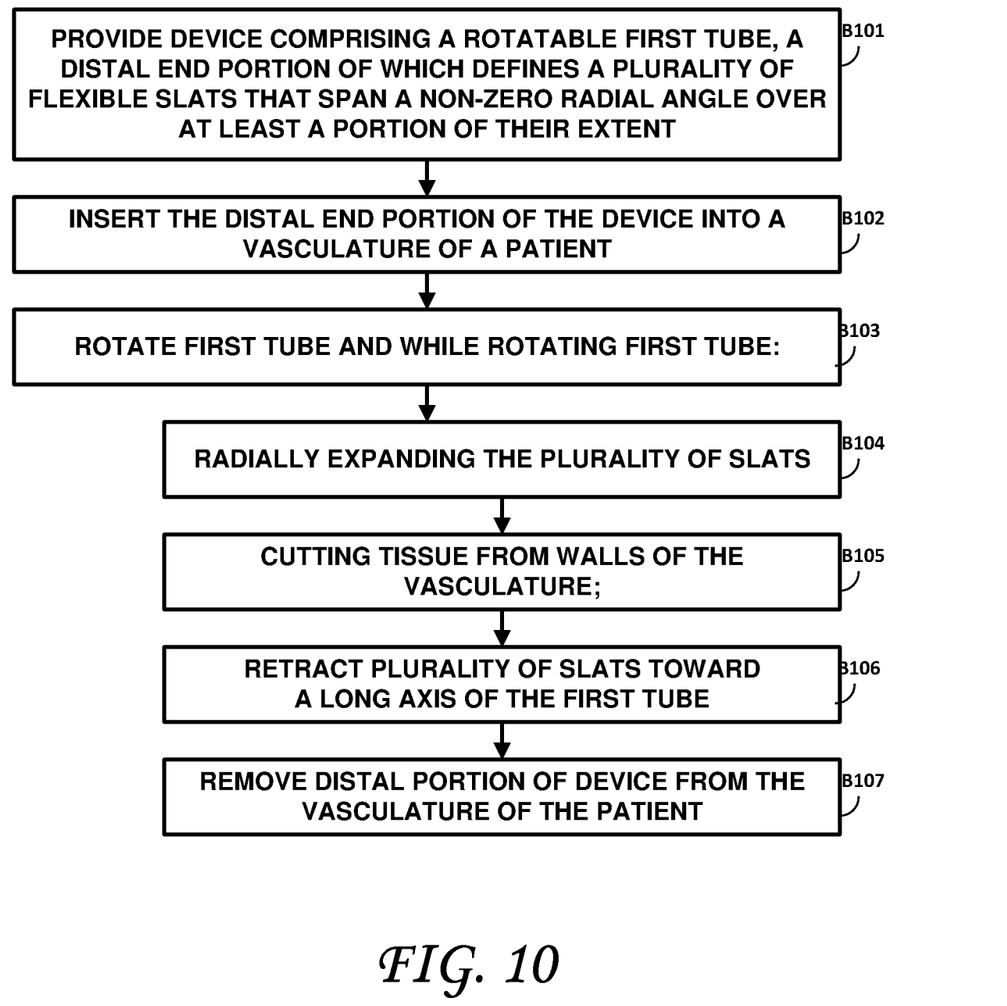
FIG. 10 is a flowchart of a method according to an embodiment.

One embodiment is a method as shown at FIG. 10. As shown therein, block B101 calls for providing a device comprising a rotatable first tube, a distal end portion of which defines a plurality of flexible slats that span a non-zero radial angle over at least a portion of their extent. The distal end portion of the device may then be inserted into a vasculature of a patient, as shown at B102. As shown at B103, the first tube may then be rotated (if it is not already rotating) and, while the first tube is rotating, one or more of B104-B107 may be performed. As shown at B104, the plurality of slats may be radially expanded. Tissue may then be cut from walls of the vasculature as shown at B105. Thereafter, the plurality of slats may be retracted toward a long axis of the first tube, as called for by B106 and the distal end portion of the device may then be removed from the vasculature of the patient. In one embodiment, at least a proximal portion of each of the plurality of slats may be configured to be drawn distally until a proximal portion of each of the plurality of slats defines an angle of less than 90 degrees with a corresponding distal portion thereof.

According to embodiments, a device 10 may be introduced intra-vascularly over a guide wire 18, which may be fixed or of a monorail "Rx" (rapid exchange) structure. According to one embodiment, the device 10, in its resting form, may present an extremely low profile, making the device 10 readily introducible into a distal vessel. Such a distal vessel may be small and/or lined with fragile thrombus or plaque. The device 10 may be introduced into a distal vessel for protection against embolic events, or it may be placed into an area of active clotting to prevent further clotting and to retrieve the majority of the clot, while allowing in-thrombus and distal injection of clot buster pharmacologic materials. According to one embodiment, device 10 may be configured to actively and/or passively return to its resting low profile. In other embodiments, the device 10 may also be configured to collect thrombotic material and not return all the way to its resting low profile. In still other embodiments, clot material and other particulates may be vacuumed out such that a resting or near resting (smallest initial outside diameter) may be achieved after the thrombotic material has been cut. Device 10 may be positively controlled to expand and contract, and may also be configured to compress in length or lengthen in order to deploy and to capture thrombus/embolic matter definitively and safely during removal. Work element 13 of device 10 may be formed of or comprise shape memory materials or alloys that assume certain configurations when a source of heat is applied thereto. The work element, according to further embodiments, may comprise bimetallic materials configured to deform and to return to an initial, resting state. According to embodiments, the device 10 may cover more than a single line of radially disposed contact points in a vascular structure, and may function effectively in tortuous or irregularly-walled vessels as well as in smooth straight blood vessels. Device 10 may also allow flow to side branch blood vessels, which are ideally also protected while blood flows are established and maintained in a main branch vessel, in spite of the lesser need for unconstrained blood flow that may be encountered vis-A-vis a main vessel. According to one embodiment, device 10 may comprise a flexible outer tube coating configured to function as a netting mechanism when such an outer tube is deployed in expanded form, or have very small perforations to allow a limited but acceptable amount of blood to flow to branch vessels.

According to one embodiment, the device 10 may be configured to be easily retrievable in its collapsed state, whether in its initial, resting fully low-profile configuration or a nearly low profile state. This ensures safe removal of the device, even in situations where the clot burden may be extremely high and in cases in which it is desired to completely remove the device 10 from the body in order to empty it of its contents, such as may occur when aspiration is not present or utilized. The device 10 may incorporate features to provide a wide open flow accommodation pathway for the main artery, which pathway may be centrally located in the central lumen of device 10 and may also be augmented by flow through other spaces. Such a central lumen flow pathway may be configured to prevent clot elements or other particulates from being admitted therein. This may be accomplished by managing flow dynamics, as illustrated in the figures above, shielding, or any combination of the management of flow dynamic and shielding, according to embodiments. The device 10 may be provided, according to embodiments, with deflectors for flow management, which may rely on a natural venture shape to capture debris as it fills up the distal capture area. Such embodiments are considered as being included in this description.

According to one embodiment, a guide wire may be left in place when device 10 is removed or exchanged. According to one embodiment, a fixed guide wire incorporated into device 10 may be removed with the device or left in place. According to embodiments, device 10 may be configured to enable injection of blood thinners, such as heparin, or clot busters, such as urokinase and others, and may further accommodate the use of platelet inhibitors, vasodilators, cooling fluids and oxygen carrier materials or medications. Device 10 may be configured to be compatible for use with other interventional devices and may be manufactured with extremely small diameters, such as 0.038", or other desired dimension.

It is to be understood that the above descriptions are but exemplary embodiments, principles and methodologies and that one or more of the interventional steps or considerations described above may be omitted, while others may be added thereto, depending on the target site within the body or other operator methodologies. The order of some of the steps may be changed, according to the vascular interventional procedure.

The described embodiments may be formed of or comprise one or more biocompatible materials such as, for example, stainless steel or other biocompatible alloys, shape memory alloys including for example bimetallics and may be made of, comprise or be coated with polymers and/or biopolymer materials as needed to optimize function(s). For example, the cutting elements (such as the constituent elements of a work element 13 or nosecone 15) may comprise or be made of hardened alloys, or carbon fiber or PEEK or other polymers or plastics, and may be additionally coated with a slippery material or materials to thereby optimize passage through living tissues of a variety of consistencies and frictions. Some of the components may be purposely surface-treated differentially with respect to adjacent components. The various internal or external components may be made of any suitable, commercially available materials such as nylons, polymers such as moldable plastics, and others. The handle may be configured to render it adaptable to one of any number of existing guiding platforms, such as stereotactic table stages. The materials used in the present device may also be carefully selected from a ferro-magnetic standpoint, such that the present material delivery or removal device maintains compatibility with magnetic resonance imaging (MRI) equipment that is commonly used for material delivery or removal procedures. Vacuum/delivery assembly components may comprise commercially available vacuum pumps, syringes and tubing for connecting to the present device, along with readily available reed valves for switching between suction and emptying of materials such as fluids, which may be suctioned by vacuum components. The fluids collected by the embodiments of the present device in this manner may then be ejected into an additional external, yet portable, liquid storage vessel connected to the tubing of the present device, for safe keeping and laboratory cellular analysis.

While certain embodiments of the disclosure have been described, these embodiments have been presented by way of example only, and are not intended to limit the scope of the disclosure. Indeed, the novel methods, devices and systems described herein may be embodied in a variety of other forms. Furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure. For example, those skilled in the art will appreciate that in various embodiments, the actual physical and logical structures may differ from those shown in the figures. Depending on the embodiment, certain steps described in the example above may be removed, and others may be added. Also, the features and attributes of the specific embodiments disclosed above may be combined in different ways to form additional embodiments, all of which fall within the scope of the present disclosure. Although the present disclosure provides certain preferred embodiments and applications, other embodiments that are apparent to those of ordinary skill in the art, including embodiments, which do not provide all of the features and advantages set forth herein, are also within the scope of this disclosure. Accordingly, the scope of the present disclosure is intended to be defined only by reference to the appended claims.

What is claimed is:

1. A method, comprising:
providing a device comprising a rotatable first tube, a distal end portion of which defines a plurality of flexible slats that span a non-zero radial angle over at least a portion of their extent, the device further comprising a second tube, the second tube being coupled to proximal ends of the plurality of slats and being configured to move distally within the first tube;
inserting the distal end portion of the device into a vasculature of a patient;
while rotating the first tube:
imparting a distally-directed movement to the second tube to radially expand the plurality of slats away from the second tube such that constituent ones of the plurality of slats, at least in their radially expanded state, do not cross over each other and such that each of the plurality of slats is aligned with a longitudinal axis of the rotatable first tube over an entire length of each of the plurality of slats; and
cutting tissue from walls of the vasculature;
imparting a further distally-directed movement to the second tube to cause the plurality of slats to expand further away from the second tube until a proximal portion of each the plurality of slats buckles and inverts back toward the second tube;
retracting the plurality of slats toward a long axis of the first tube; and
removing the distal end portion of the device from the vasculature of the patient.

2. The method of claim 1, wherein at least a proximal portion of each of the plurality of slats is configured to be drawn distally until a proximal portion of each of the plurality of slats defines an angle of less than 90 degrees with a corresponding distal portion thereof.

3. The method of claim 1, wherein providing is carried out with the plurality of flexible slats being formed by cuts in the distal end portion of the rotatable first tube.

4. The method of claim 1, wherein inserting is carried out with the plurality of flexible slats being in a twisted spiral configuration, and disposed close to a longitudinal axis of the rotatable first tube.

5. The method of claim 1, wherein cutting is carried out with each of the plurality of slats comprising a leading sharp edge.

6. The method of claim 1, wherein the plurality of slats are coupled to a distal nose cone and wherein radially expanding the plurality of slats comprises differentially rotating the distal nose cone relative to the first tube or differentially rotating of the first tube relative to the distal nose cone, to cause radial movement of the plurality of slats.

7. The method of claim 1, further comprising selectively bowing the plurality of slats radially outward and radially inward between the proximal end of the work element and the distal end of the work element.

8. The method of claim 1, wherein radially expanding and retracting are carried out by applying respective torsional forces to the first tube.

9. The method of claim 1, wherein imparting a further distally-directed movement to the second tube causes the proximal portion of each of the plurality of slats to assume an angle of less than 90 degrees with a corresponding distal portion thereof.

10. The method of claim 1, wherein imparting a further distally-directed movement to the second tube causes at least the proximal portion of each of the plurality of slats to be drawn toward the distal end of the work element until a circumferential rim is formed.

11. The method of claim 1, wherein providing is carried out with each of the plurality of slats forming a living hinge formed from the first tube.

12. The method of claim 1, wherein providing further comprises configuring the providing device as an embolectomy device.

13. The method of claim 1, wherein providing further comprises configuring the providing device as a thromboembolic protective device.

14. The method of claim 1, wherein providing further comprises configuring the providing device as an atherectomy device.

15. The method of claim 1, wherein inserting the distal end portion of the device into a vasculature of a patient further comprises enabling blood flow at least from a point distal to the work element to a point proximal thereto.

16. The method of claim 1, wherein retracting the plurality of slats toward a long axis of the first tube is carried out with the retracted slats wrapped around the cut tissue.

17. A method, comprising:
provide a device comprising:
a rotatable first tube, a distal end portion of which defines a plurality of flexible slats that span a non-zero radial angle over at least a portion of their extent;
a second tube, the second tube being coupled to proximal ends of the plurality of slats and being configured to move distally within the first tube;
inserting the distal end portion of the device into a vasculature of a patient;
while rotating the first tube:
radially expanding the plurality of slats by imparting a distally-directed movement to the second tube to cause the plurality of slats to selectively expand away from the second tube;
cutting tissue from walls of the vasculature;
imparting a further distally-directed movement to the second tube to cause the plurality of slats to expand further away from the second tube until a proximal portion of each the plurality of slats buckles and inverts back toward the second tube;
retracting the plurality of slats toward a long axis of the first tube; and
removing the distal end portion of the device from the vasculature of the patient.

18. The method of claim 17, wherein imparting a further distally-directed movement to the second tube causes the proximal portion of each of the plurality of slats to assume an angle of less than 90 degrees with a corresponding distal portion thereof.

19. The method of claim 17, wherein imparting a further distally-directed movement to the second tube causes at least the proximal portion of each of the plurality of slats to be drawn toward the distal end of the work element until a circumferential rim is formed.

* * * * *